US009134330B2

(12) United States Patent
Maeba et al.

(10) Patent No.: US 9,134,330 B2
(45) Date of Patent: Sep. 15, 2015

(54) DETECTION METHOD

(75) Inventors: Ryouta Maeba, Tokyo (JP); Hiroshi Hara, Hokkaido (JP); Megumi Nishimukai, Hokkaido (JP); Yuya Yamazaki, Tokyo (JP); Toru Nezu, Tokyo (JP)

(73) Assignees: TEIKYO UNIVERSITY, Tokyo (JP); NATIONAL UNIVERSITY CORPORATION HOKKAIDO UNIVERSITY, Hokkaido (JP); ADEKA CORPORATION, Tokyo (JP)

( * ) Notice: Subject to any disclaimer, the term of this patent is extended or adjusted under 35 U.S.C. 154(b) by 192 days.

(21) Appl. No.: 13/701,918

(22) PCT Filed: Jun. 3, 2011

(86) PCT No.: PCT/JP2011/062799

§ 371 (c)(1), (2), (4) Date: Apr. 23, 2013

(87) PCT Pub. No.: WO2011/152519

PCT Pub. Date: Dec. 8, 2011

(65) Prior Publication Data

US 2013/0203176 A1 Aug. 8, 2013

(30) Foreign Application Priority Data

Jun. 4, 2010 (JP) ................................. 2010-129169

(51) Int. Cl.
*G01N 33/92* (2006.01)
*G01N 33/48* (2006.01)

(52) U.S. Cl.
CPC ................ *G01N 33/92* (2013.01); *G01N 33/48* (2013.01); *G01N 2800/042* (2013.01); *G01N 2800/044* (2013.01); *G01N 2800/321* (2013.01); *G01N 2800/323* (2013.01)

(58) Field of Classification Search
CPC ... G01N 33/48; G01N 33/92; G01N 2800/00; G01N 2800/042; G01N 2800/044; G01N 2800/32; G01N 2800/321; G01N 2800/323; G01N 2800/324; G01N 2800/325; G01N 2800/50; G01N 2800/52; G01N 2800/60
USPC .................... 436/63, 71, 103, 127, 161, 173; 422/430; 554/80; 558/86
See application file for complete search history.

(56) References Cited

U.S. PATENT DOCUMENTS

| | | | | |
|---|---|---|---|---|
| 6,830,932 | B1 | 12/2004 | Danne et al. | |
| 2005/0112675 | A1 | 5/2005 | Kochan et al. | |
| 2008/0020472 | A1 | 1/2008 | Shan et al. | |
| 2009/0318392 | A1 * | 12/2009 | Oresic et al. | 514/114 |

FOREIGN PATENT DOCUMENTS

| | | | |
|---|---|---|---|
| CN | 1619312 | A | 5/2005 |
| EP | 1533619 | B1 | 4/2009 |
| JP | 2001-178489 | * | 7/2001 |
| JP | 2007-033410 | A | 2/2007 |
| JP | 2009-269865 | A | 11/2009 |
| JP | 2011-136926 | * | 7/2011 |
| WO | 03/005628 | A2 | 1/2003 |

OTHER PUBLICATIONS

Ryota Maeba, "Michi nam Phospholipid—Plasmalogen-", Oleoscience, 2005, vol. 5, No. 9, pp. 405-415.

Ryota Maeba et al., "Capillary Tosoku Denki Eidoho o Mochiita Liprprotein Buseki no Metabolic Syndrome no Rinsho Shindan ni Okeru Yuyosei", Seibutsu Shiryo Bunseki, 2007, vol. 30, No. 2, pp. 150-156.

Ryota Maeba et al., "Myo-Inositol Treatment Increases Serum Plasmalogens and Decreases Small Denses LDL, Particularly in Hypderlipidemic Subjects with Metabolic Syndrome", J.Nutru.Sci. Vitaminol., 2008, vol. 54, No. 3, pp. 196-202.

Ryota Maeba et al., "Plasmalogens in Human Serum Positively Correalte with Hihg-Density Lipoprotein and Decrease with Aging", J.Atheroscler.Throm., 2007, vol. 14, No. 1, pp. 12-18.

S. Kobayashi et al., "Synthesis of 1-O-Acylglycerol 2,3-Cyclic Phosphate: Determination of the Absolute Structure of PHYLPA, A specific Inhibitor of DNA Polymerase alpha.", Tetrahedron Left., 1993, vol. 34, No. 25, pp. 4047-4050.

* cited by examiner

*Primary Examiner* — Maureen Wallenhorst

(74) *Attorney, Agent, or Firm* — Heslin Rothenberg Farley & Mesiti P.C.

(57) ABSTRACT

The object of the present invention is to provide a biomarker which is highly correlated to the conventional biomarkers of metabolic syndrome or life-style related disease in a wide range of subjects to be tested, including subjects of special health check-up aged between 40 and 74, or an advantageous method for detecting metabolic syndrome or life-style related disease. The object can be solved by a method for detecting metabolic syndrome or life-style related disease by measuring the concentration of choline plasmalogen in a sample to be tested.

6 Claims, No Drawings

DETECTION METHOD

CROSS REFERENCE TO RELATED APPLICATION

This application is the National Phase filing of International Application No. PCT/JP2011/062799, filed Jun. 3, 2011, which claims priority to Japanese Application No. 2010-129169, filed Jun. 4, 2010. The entire content of each prior application is hereby incorporated by reference.

TECHNICAL FIELD

The present invention is related to a method for detecting metabolic syndrome or life-style related disease and a kit for detecting metabolic syndrome or life-style related disease.

BACKGROUND ART

Recently, it is known that the life-style related diseases such as arteriosclerosis, hyperlipemia, diabetes, hypertension, and central obesity, are developed based on a common metabolic abnormality, which has been referred to as a metabolic syndrome. According to the Ordinance of the Ministry of Health, Labour and Welfare No. 157 "Practice guideline for special health checkups and special health-maintenance guidance (Dec. 28, 2007)", a special health check-up was given to insured persons aged between 40 and 74. Examinations of waist circumference, blood pressure, serum triglyceride (neutral fat) level, high-density lipoprotein cholesterol (HDL-C) level, and blood glucose were carried out from April, 2008. As health guidance is given to the persons diagnosed with metabolic syndrome, health awareness in people has been increased. Thus, it is becoming popular to prevent life-style related disease in a positive manner.

Hitherto, as a risk marker for development of arteriosclerosis, high-density lipoprotein cholesterol (HDL-C) level, low-density lipoprotein cholesterol (LDL-C) level, small, dense LDL (sdLDL), apolipoprotein A, adiponectin, CRP (C-reactive Protein), and AIP (Atherogenic Index of Plasma), and the like are known.

sdLDL is a LDL which contains a high proportion of triglyceride, and has a smaller particle size than normal LDL. sdLDL is more susceptible to oxidation compared to normal LDL, and it is known that sdLDL strongly causes the development of arteriosclerosis. Apolipoprotein A constitutes HDL, and promotes the removal of cholesterol from cells. Adiponectin is a hormone released from adipocyte, and it is known that adiponectin exhibits functions to promote insulin sensitivity, prevent arteriosclerosis, and inhibit inflammation. Further, the blood concentration of adiponectin is negatively correlated with the amount of visceral fat. CRP is produced when an inflammatory reaction is developed in the body. CRP has attracted attention as a marker of arteriosclerosis with a chronic vascular inflammation. AIP is an index in serum for arteriosclerosis which is calculated by a formula, "log (triglyceride concentration/HDL-C concentration)", using a triglyceride concentration and HDL-C concentration.

Further, it is said that oxidation of LDL is the greatest contributor to the development of arteriosclerosis. LDL which is oxidized through abnormalities of metabolism or transport of cholesterol, leads to a conversion of macrophages to foam cells, and induces the production of superoxide from neutrophil, whereby the oxidized LDL further induces lipid peroxidation and lipid accumulation at vascular subendothelium so as to progress arteriosclerosis. Therefore, in order to prevent the development of arteriosclerosis, it is remarkably effective to inhibit the oxidation of LDL.

Plasmalogen is a kind of glycerophospholipid, and has an olefinyl chain (vinyl ether bond) at the sn-1 position, an acyl chain at the sn-2 position, and a base-bound phosphoric acid at the sn-3 position of the glycerol backbone. In the plasmalogen present in a living body, the number of carbon atoms of the major olefinyl chain is 16 to 18, and the major acyl chain is a fatty acid having 16 to 22 carbon atoms. The major base bound to phosphoric acid is choline or ethanolamine, and the corresponding plasmalogens are referred to as choline plasmalogen (hereinafter sometimes referred to as a "CP") or ethanolamine plasmalogen (hereinafter sometimes referred to as an "EP"), respectively. It is known that the proportion of CP is high in the heart and skeletal muscle of mammals, and a proportion of EP is high in the brain and kidneys of mammals.

The concentration of phospholipids in human plasma is 2 to 3 mM, and the phospholipids are contained therein as a constituent of lipoprotein. 60 to 75% of the total phospholipids are choline glycerophospholipid, 2 to 5% thereof are ethanolamine glycerophospholipid, and 10 to 20% thereof are sphingomyelin phospholipid.

The concentration of plasmalogen in human plasma is 0.1 to 0.3 mM, and proportions of CP and EP are 40% and 60% respectively. That is, about 5% of choline glycerophospholipid and about 60% of ethanolamine glycerophospholipid are plasmalogen, and there are very few plasmalogen having a base other than choline and ethanolamine, in blood.

Reported physiological roles of plasmalogen are: a function of membrane fusion in cell fusion or secretory action, an involvement in signal transduction or transport of biological macromolecule, a role as a reservoir of polyunsaturated fatty acid which is easily oxidized, and a role as an endogenous antioxidant. Further, it is reported that an inherited plasmalogen deficiency in humans exhibits symptoms of profound mental retardation, adrenal disorder, cataracts, hearing disorder, stunted growth, or the like. It is also reported that the serum plasmalogen level in Alzheimer's disease patients and aged persons is decreased. These findings suggest that plasmalogen plays an important role in the body (non-patent literature 1). In addition, it is known that plasmalogen synthesized in liver is preferentially incorporated into lipoprotein component. Furthermore, it is considered that plasmalogen acts as an antioxidative factor for LDL due to the endogenous antioxidant activity thereof.

Patent literature 1 discloses that choline plasmalogen level and ethanolamine plasmalogen level in the blood of persons of middle or advanced age including hyperlipemia patients were measured, and the CP/EP ratio is significantly correlated to fasting triglyceride level, which means the neutral fat level, and LDL size, which means the sdLDL level, respectively (the corresponding correlation coefficients are −0.359 and 0.402 respectively). Further, patent literature 1 discloses that the CP/EP ratio can be used as a biomarker for preventing life-style related disease. In addition, non-patent literature 1 discloses that the amount of total CP or the amount of total EP is correlated to HDL-C, apolipoprotein A-I, and apolipoprotein A-II (the correlation coefficients are more than 0.28).

However, the correlations between the CP/EP ratio and fasting triglyceride (neutral fat) or LDL size (sdLDL), disclosed in patent literature 1; and the correlations between the total CP amount or the total EP amount and HDL-C, apolipoprotein A-I, or apolipoprotein A-II disclosed in non-patent literature 1, are not sufficiently strong, and therefore these biomarkers for detecting life-style related disease are by no means satisfactory.

PATENT LITERATURE

[Patent literature 1] Japanese Unexamined Patent Publication (Kokai) No. 2007-33410

NON-PATENT LITERATURE

[Non-patent literature 1] Journal of Atherosclerosis and Thrombosis, 2007, Japan, vol. 14, p. 12-18

SUMMARY OF INVENTION

Technical Problem

Patent literature 1 discloses that clinical test items, i.e. presence or absence of coronary stenosis, abnormal glucose tolerance, significant stenosis, age, sex, CAG, OGTT, hyperlipemia, abnormal glucose tolerance, body height, body weight, BMI, cigarette smoking (number of cigarette smoked per day, duration of smoking), family history, hypertension, gout, or the like are tested, and clinical measurement items, i.e. plasmalogen level in plasma, uric acid level, TC, TG (fasting), HDL, LDL, FBS, HbA1c, TC__2, TG__2, HDL__2, LDL__2, apoprotein A-I, apoprotein A-II, apoprotein B, apoprotein C-II, apoprotein apoprotein E, LP(A), LP-F_PGR, lipoprotein α (HDL), lipoprotein β (LDL), lipoprotein preβ (VLDL), RLP-C, S__0', S__120', IRI__0', IRI__120', IRI__0', IRI__120', HOMA_IR, LPL, adiponectin, MDA_LDL, LPL following heparin treatment, fasting ApoB48, postprandial ApoB48 LDL size, phospholipid level, choline plasmalogen (CP), ethanolamine plasmalogen (EP), CP/EP, or the like, are measured, and then the correlations among clinical parameters and biochemical data were examined. Further, patent literature 1 discloses that fasting triglyceride level (TG), $HDL_2$ level, or CP/EP value is significantly correlated to LDL size, and as mentioned above, CP/EP value is significantly correlated to fasting triglyceride level (TG). However, patent literature 1 does not disclose correlations between items other than the above items.

As mentioned above, in patent literature 1, statistically-significant correlations between CP/EP ratio and fasting triglyceride (neutral fat) level, and between CP/EP ratio and sdLDL, are described. However, the correlation coefficients thereof are −0.359 and 0.402, respectively, which are somewhat low. Further, in non-patent literature 1, the correlation coefficients between total CP level, and HDL-C, apolipoprotein A-I, or apolipoprotein A-II are 0.308, 0.435, or 0.241, which are not very high.

The reason for this is presumed to be as follows. In patent literature 1 and non-patent literature 1, the method for measuring a plasmalogen level in the blood is a method wherein a radioactive iodine is specifically bound to plasmalogens contained in lipid components by reacting extracted lipids with a triiodide ion, and the resulting plasmalogens are fractionated into CP and EP, and measured by chromatography. The accuracy of the above method is not sufficient due to the effects of radioactive decay, or the like. That is, the use of radioactive iodine is one of the reasons that accuracy is insufficient.

Further, on the method for measuring plasmalogen in patent literature 1 and non-patent literature 1, an internal standard material is not used. Therefore, obtained measurement values are variable between measurement tests, measurement dates, and measurers, whereby there may be a possibility that the above correlation coefficients are reduced.

Accordingly, the object of the present invention is to provide a biomarker which is highly correlated to the conventional biomarkers of metabolic syndrome or life-style related disease in a wide range of subjects including subjects of special health check-ups aged between 40 and 74, or an advantageous method for detecting metabolic syndrome or life-style related disease. Further, the object of the present invention is to provide a biomarker capable of determining the risk or degree of seriousness of metabolic syndrome or life-style related disease, and a method for analyzing the risk or degree of seriousness of metabolic syndrome or life-style related disease.

Solution to Problem

With the aim of solving the aforementioned problems, the present inventors have conducted intensive studies into a method for analyzing plasmalogen capable of quantifying blood plasmalogen level with greater accuracy, and as a result, found that the method described in patent literature 1 can be much improved by using 1-alkenyl cyclic phosphatidic acid (1-alk-1'-enyl-sn-glycerol-2,3-cyclic phosphate; hereinafter sometimes referred to as a cAP) as an internal standard material, resulting in a method with greater accuracy. Further, the present inventors found that it is possible to analyze a fatty acid bound at the sn-2 position of CP (i.e. molecular species of CP) with high accuracy, by using a synthetic choline plasmalogen as the internal standard, and by analyzing plasmalogen using liquid chromatography-tandem mass spectrometer (hereinafter referred to as a LC-MS/MS) mass spectrometer (hereinafter referred to as a LC-MS/MS)

451 subjects aged from their 20s and their 60s, not including severe patients, are examined by means of the above two analyzing methods using the internal standard. As a result, compared to the amount of total serum plasmalogen, the amount of CP, particularly the amount of a CP in which the fatty acid bound at the sn-2 position is oleic acid (hereinafter referred to as a C18:1 CP), or the amount of a CP in which the fatty acid bound at the sn-2 position is linoleic acid (hereinafter referred to as a C18:2 CP) is strongly correlated to arteriosclerosis-related factors, such as waist circumference, adiponectin, or AIP, as well as HDL-C, triglyceride, or sdLDL.

In addition, the present inventor found that the ratio of CP to total phospholipids (hereinafter referred to as a "CP/PL ratio") is more strongly correlated to the above arteriosclerosis-related factors, than the CP itself is.

The present inventor also found that a ratio of CP to body weight (hereinafter referred to as a "CP/body weight ratio"), or a ratio of CP to triglyceride (hereinafter referred to as a "CP/triglyceride ratio") is more strongly correlated to the above arteriosclerosis-related factors, than the CP itself is.

Correlation coefficients between each of the above three ratios and each measurement item are higher than those between the CP/EP ratio which is the biomarker disclosed in patent literature 1, and each measurement item, and the above three ratios are correlated to more measurement items than the CP/EP ratio. In particular, as the above three ratios are correlated to waist circumference or adiponectin which are obesity-related factor, it was found that these ratios are highly effective as a biomarker which can be correlated to overall disorder of lipid metabolism.

Namely, the present invention relates to:

[1] a method for detecting metabolic syndrome or life-style related disease characterized by comprising the step of measuring the concentration of choline plasmalogen in a sample to be tested,

[2] the method for detecting metabolic syndrome or life-style related disease of the item [1], wherein the choline plasmalogen is a choline plasmalogen having oleic acid at the sn-2 position or a choline plasmalogen having linoleic acid at the sn-2 position,

[3] the method for detecting metabolic syndrome or life-style related disease of the item [1] or [2], further comprising the steps of measuring at least one value selected from the group consisting of: the phospholipid concentration in the sample to be tested, the triglyceride concentration in the sample to be tested, and the body weight of the subject; and calculating the ratio of the value of choline plasmalogen concentration, to the phospholipid concentration in the sample to be tested, the triglyceride concentration in the sample to be tested, or a value of body weight of the subject

[4] the method for detecting metabolic syndrome or life-style related disease of any one of the items [1] to [3], the life-style related disease is selected from the group consisting of dyslipidemia, hypertension, and arteriosclerosis,

[5] the method for detecting metabolic syndrome or life-style related disease of any one of items [1] to [3], wherein the method is for preventing development of metabolic syndrome or life-style related disease, or monitoring a treatment effect against metabolic syndrome or life-style related disease,

[6] the method for detecting metabolic syndrome or life-style related disease of any one of items [1] to [5], wherein at least one compound selected from the group consisting of 1-alkenyl cyclic phosphatidic acid of the general formula (1):

[Chem. 1]

(1)

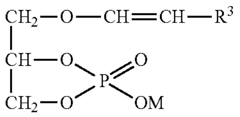

wherein $R^3$ is an alkyl group having 4 to 26 carbon atoms or an alkenyl group having 4 to 26 carbon atoms, and M is a hydrogen atom or a counter cation, and a compound of the general formula (2):

[Chem. 2]

(2)

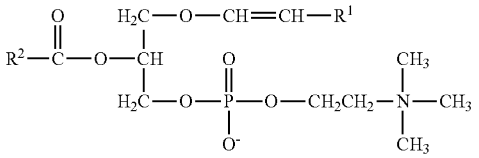

wherein $R^1$ is an alkyl group having 7, 9, 11, 13, 15, 17, 19, or 21 carbon atoms, and $R^2$ is an alkyl group having 8 to 21 carbon atoms or an alkenyl group having 8 to 21 carbon atoms, is used as an internal standard material for analyzing plasmalogen,

[7] a kit for detecting metabolic syndrome or life-style related disease, characterized by comprising a 1-alkenyl cyclic phosphatidic acid of the general formula (1):

(1)

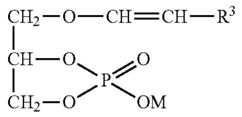

wherein $R^3$ is an alkyl group having 4 to 26 carbon atoms or an alkenyl group having 4 to 26 carbon atoms, and M is a hydrogen atom or a counter cation, as an internal standard material for analyzing plasmalogen, and

[8] a kit for detecting metabolic syndrome or life-style related disease, characterized by comprising a compound of the general formula (2):

[Chem. 4]

(2)

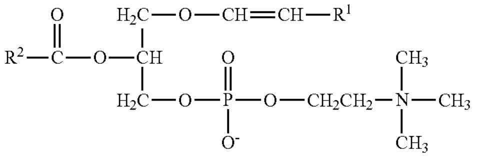

wherein $R^1$ is an alkyl group having 7, 9, 11, 13, 15, 17, 19, or 21 carbon atoms, and $R^2$ is an alkyl group having 8 to 21 carbon atoms or an alkenyl group having 8 to 21 carbon atoms, as an internal standard material for analyzing plasmalogen.

Advantageous Effects of Invention

According to the method or kit for detecting metabolic syndrome or life-style related disease, metabolic syndrome or life-style related disease can be detected at high detection rates, compared to the conventional method or kit. In particular, metabolic syndrome can be detected at high rates. Further, the measurement value obtained by the detection method or detection kit of the present invention is highly correlated to the biomarkers of life-style related disease i.e. it is a measurement value of HDL-C, sdLDL, AIP, waist circumference, body weight, or adiponectin. Furthermore, in the method or kit for detecting metabolic syndrome or life-style related disease, the use of 1-alkenyl cyclic phosphatidic acid or synthetic choline plasmalogen as an internal standard makes it possible to accurately measure the amount of choline plasmalogen, and further makes it possible to accurately analyze molecular species of choline plasmalogens.

Therefore, the detection method or the detection kit of the present invention can diagnose the risk or degree of seriousness of metabolic syndrome or life-style related disease, more accurately than ever before. A biomarker founded by the present inventor more accurately shows the risk or degree of seriousness of metabolic syndrome or life-style related disease, compared to conventional biomarkers.

DESCRIPTION OF EMBODIMENTS

[1] Method for Detecting Metabolic Syndrome or Life-Style Related Disease

The method for detecting metabolic syndrome or life-style related disease of the present invention comprises the step of measuring the concentration of choline plasmalogen in a sample to be tested. The method for detecting metabolic syndrome or life-style related disease of the present invention can be used for diagnosing metabolic syndrome or life-style related disease. The method for diagnosing metabolic syndrome or life-style related disease is an in vitro diagnostic method. That is, the diagnostic method comprises the step of in vitro measurement of choline plasmalogen contained in the sample isolated from mammals including humans.

In the detection method of the present invention, the total amount of choline plasmalogen or concentrations of molecular species of choline plasmalogen is measured. If the total amount of choline plasmalogen or the concentrations of molecular species of choline plasmalogen is analyzed and measured without adding an internal standard to the sample, it is impossible to correct for variations of extraction efficiencies between samples, or variations of ionization efficiencies between sample injections to the mass spectrometer, which are normally-occurring on the analysis. Therefore, in order to correct the above variations, an internal standard is added to sample. Hitherto, cholic acid, or the like is used as the internal standard. However, the polar character and the ionization efficiency of cholic acid are very different from those of choline plasmalogen, and thus it cannot be said that the measurement values thereof are accurate values of the plasmalogen amount.

The present inventors found that it is possible to measure accurately the amount of choline plasmalogen in the sample by using 1-alkenyl cyclic phosphatidic acid (1-alk-1'-enyl-sn-glycerol-2,3-cyclic phosphate; hereinafter, sometimes referred to as a cAP) or synthetic choline plasmalogen as a novel internal standard material. 1-alk-1'-enyl-sn-glycerol-2,3-cyclic phosphate and synthetic choline plasmalogen which may be used as the internal standard in the present invention, will be explained in detail hereinafter.

<<Internal Standard Material>>

(1-Alkenyl Cyclic Phosphatidic Acid)

In the detection method of the present invention, 1-alkenyl cyclic phosphatidic acid (cAP) which may be used as the internal standard, is a compound of the general formula (1):

[Chem. 3]

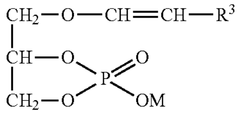

(1)

wherein $R^3$ is an alkyl group having 4 to 26 carbon atoms or an alkenyl group having 4 to 26 carbon atoms, and M is a hydrogen atom or a counter cation.

In the 1-alkenyl cyclic phosphatidic acid, $R^3$ is an alkyl group or an alkenyl group having 4 to 26 carbon atoms, preferably an alkyl group or an alkenyl group having 8 to 22 carbon atoms, more preferably an alkyl group or an alkenyl group having 12 to 18 carbon atoms and most preferably an alkyl group or an alkenyl group having 14 to 16 carbon atoms. Further, as the $R^3$, an alkyl group is more preferable than an alkenyl group. Most side chains of plasmalogen at the sn-1 position are hydrocarbon groups having vinyl ether bonds of 16:0, 18:0, and 18:1. Therefore, if $R^3$ is an alkyl group having 3 or fewer, or 27 or more carbon atoms, there is a possibility that the behavior of the 1-alkenyl cyclic phosphatidic acid having such $R^3$ is different from that of plasmalogen in vivo. Thus, 1-alkenyl cyclic phosphatidic acid having 3 or fewer, or 27 or more carbon atoms, is not preferable.

The cAP can be prepared by a chemical synthetic procedure or an enzymatic synthesis procedure. The enzymatic synthesis procedure can be carried out in accordance with a method described in Japanese Unexamined Patent Publication (Kokai) No. 2001-178489. Together with 1-lysophosphatidic acid plasmalogen, cAP is produced by the reaction of 1-lysoplasmalogen (for example, 1-lyso-choline plasmalogen) and phospholipase D (for example, phospholipase D derived from *Actinomadura* sp. Strain No. 362). Further, the present inventors found that 1-lysophosphatidic acid plasmalogen can be removed from the product by a re-extraction using ether/ethanol mixed solvent so as to obtain highly-pure cAP.

cAP can be used as an internal standard material in a method for measuring total CP amount as described below.

(Synthetic Choline Plasmalogen)

In the detection method of the present invention, the synthetic choline plasmalogen which may be used as the internal standard material, is a compound of the general formula (2):

[Chem. 4]

(2)

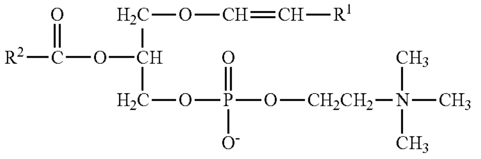

wherein $R^1$ is an alkyl group having 7, 9, 11, 13, 15, 17, 19, or 21 carbon atoms, and $R^2$ is an alkyl group having 8 to 21 carbon atoms or an alkenyl group having 8 to 21 carbon atoms.

In the synthetic choline plasmalogen, $R^1$ is an alkyl group having 7, 9, 11, 13, 15, 17, 19, or 21 carbon atoms, preferably an alkyl group having 7, 9, 11, 19, or 21 carbon atoms, more preferably an alkyl group having 7, 9, 19, or 21 carbon atoms and most preferably an alkyl group having 19 or 21 carbon atoms. Most side chains of plasmalogen at the sn-1 position are hydrocarbon groups having vinyl ether bonds of 16:0, 18:0, and 18:1, and there are very few plasmalogen with hydrocarbon groups containing odd-numbers of carbon atoms in the living body. Therefore, if the synthetic choline plasmalogen wherein $R^1$ is an alkyl group having odd-numbered carbon atoms, is used as the internal standard compound for analysis of plasmalogen, the elute position of the synthetic choline plasmalogen may be separated from those of plasmalogen in a living body, in various analysis methods. Therefore, the synthetic choline plasmalogen can be clearly distinguished from the plasmalogen in a living body.

The compound of the general formula (2) is described in a specification of Japanese patent application 2009-296744 by the present inventors. The compound can be used as the internal standard in a method for measuring plasmalogen using gas chromatography, a method for measuring plasmalogen using high-performance liquid chromatography, and a method for measuring plasmalogen using mass spectrometry. In particular, when the compound is used in a method for measuring plasmalogen using a liquid chromatography-tandem mass spectrometer, it is possible to accurately measure molecular species of choline plasmalogen.

In particular, a preferable embodiment of the synthetic choline plasmalogen includes a compound of the general formula (3):

[Chem. 5]

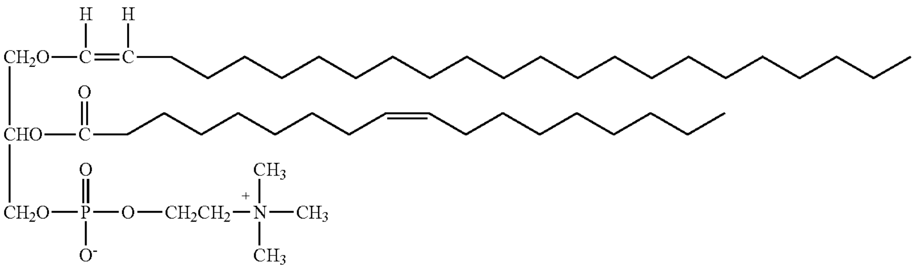

(3)

The synthetic choline plasmalogen of the general formula (3) can be prepared according to the formula of reaction process (4) shown schematically below:

[Chem. 6]

(4)

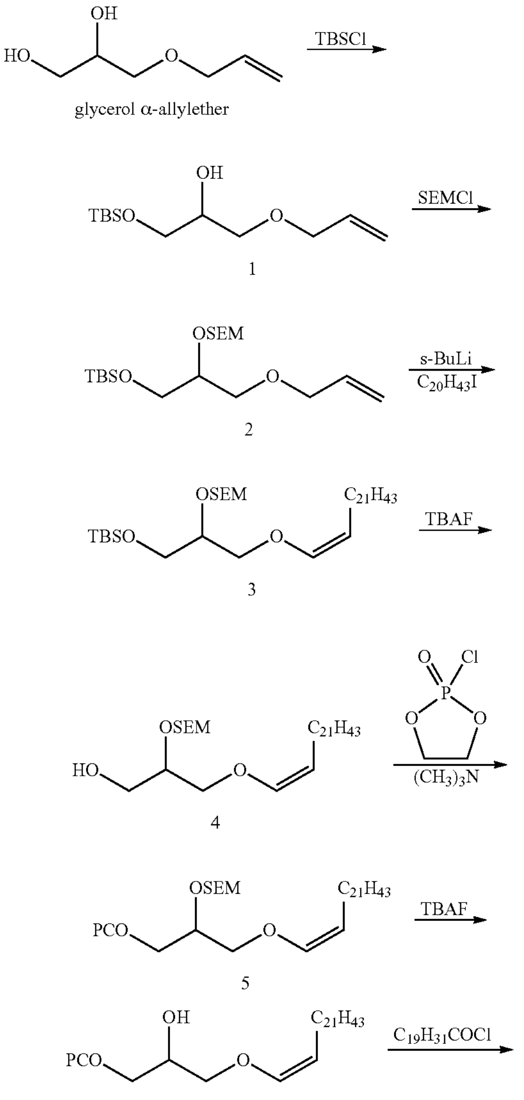

-continued

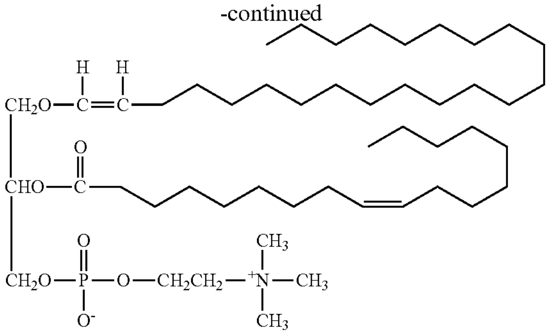

7

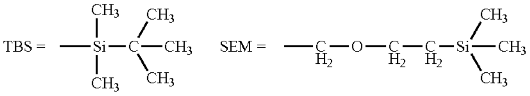

TBAF = $(n\text{-}Bu)_4NF$

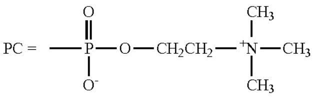

The synthetic choline plasmalogen can be used as the internal standard in a method for measuring total CP amount, and a method for measuring molecular species of CP, as mentioned below. Further, it is considered that the synthetic choline plasmalogen is more similar to the plasmalogen to be measured than cholic acid, which is conventionally used as the internal standard, in all aspects of the polar character, extraction efficiency, and ionization efficiency in a mass spectrometer. Therefore, the synthetic choline plasmalogen is superior to cholic acid as the internal standard. That is, it is possible to obtain accurate measurement values without variability of the data, by using the synthetic choline plasmalogen as the internal standard.

<<Extraction of Plasmalogen from Sample to be Tested>>

In the measurement of the concentration of plasmalogen in the detection method of the present invention, firstly plasmalogen is extracted from a sample to be tested. The method for extracting plasmalogen from sample to be tested, is not limited so long as a phospholipid can be recovered from the sample by the method, but includes Bligh & Dyer method, Folch method, a method using hexane/ethanol mixed solvent, a method using ether/ethanol mixed solvent, or a method wherein the sample is freeze dried and extracted using a solvent such as chloroform/methanol mixed solvent. Among these extraction methods, Bligh & Dyer method is complicated in its procedure, and the collection rate by the method using hexane/ethanol mixed solvent is low, and therefore, the method using ether/ethanol mixed solvent, and the method wherein the sample is freeze dried and extracted using a solvent such as chloroform/methanol mixed solvent, are preferable. Further, in the method wherein a radioactive iodine reagent is used and plasmalogen is analyzed by HPLC as mentioned below, another aqueous substance may be mixed in the extraction sample due to the freeze-dry procedure. Therefore, the method using ether/ethanol mixed solvent is preferable.

In the method using ether/ethanol mixed solvent, ether/ethanol mixed solvent is added to the sample to be tested so as to extract lipid, and then water is added to the whole so as to separate the ether layer. Then, the separated ether layer is collected as a lipid extract liquid. Specifically, 0.2 to 2.0 mL of ether (preferably, 0.5 to 1.5 mL of ether) and 1.0 to 4.0 mL of ethanol (preferably, 2.0 to 3.0 mL of ethanol) are added to 11.0 mL of sample such as serum or plasma, and the lipid therein is extracted. Here, the ether/ethanol ratio is preferably 1:2 to 1:4. Subsequently, 2.0 to 10 mL of ether and 4.0 to 10 mL of water are added to the whole so that the ether layer and the water layer are separated from each other. Here, the added ether/water ratio is preferably 1.0 to 2.5. According to the above procedure, the separated ether layer is collected as a lipid extract liquid. In order to further increase the collection rate, 2.0 to 5.0 mL of ether may be further added to the remaining water layer and the remaining lipid extracted.

The method wherein a sample is freeze dried and then lipid is extracted using chloroform/methanol mixed solvent, for example, can be carried out as follows. An obtained sample to be tested, such as plasma, is freeze-dried and 0.5 mL of a mixture of chloroform and methanol (with a ratio of chloroform to methanol of 2 to 1) is added thereto. Resulting solution is centrifuged and a supernatant (1) is collected. To the remaining lower layer, 1 mL of the mixture of chloroform and methanol (with a ratio of chloroform to methanol of 2 to 1) is added. The resulting solution is further centrifuged and a supernatant (2) is collected. The supernatants (1) and (2) are mixed, and the solvents are removed therefrom by spraying with nitrogen gas. The obtained solid body is dissolved in 1 mL of methanol so that an extracted sample containing plasmalogen is obtained.

The sample to be tested is not particularly limited, so long as it is derived from an animal, for example a human, but includes liquid samples derived from animals including humans (for example, blood, serum, plasma, lymph fluid, tissue fluid, spinal fluid, saliva, urine, tear, sudor, or the like), organ, cell, tissue, or the like. The sample to be tested is preferably blood, serum, or plasma (hereinafter sometimes referred to as blood or the like). When human plasma is used as the sample to be tested, blood is collected using a blood collection tube containing a blood coagulant such as EDTA. Then, blood cells are removed from the collected blood by a centrifugation, and the obtained supernatant may be used as the plasma. Further, when human serum is used as the sample to be tested, blood is allowed to stand at room temperature after blood withdrawal and a separated serum may be used. Furthermore, when an organ, tissue or cells are used as the sample to be tested, a sample liquid containing plasmalogen may be obtained by using an extraction liquid for organ, tissue or cells. Then, plasmalogen can be extracted from the sample liquid by using the aforementioned extraction methods.

The extracted plasmalogen may be used in the method for measuring total CP amount and the method for measuring for molecular species of CP, as described below.

<<Method for Measuring Total CP Amount>>

The method for measuring total CP amount is not particularly limited, so long as CP and EP can be measured separately by the method, but includes the method using gas chromatography, the method using high-performance liquid chromatography, and the mass spectrometry method. In particular, the method using high-performance liquid chromatography (HPLC), or the mass spectrometry method are preferable.

Hitherto, as the method for quantifying CP amount in the sample to be tested such as serum or plasma, there exist only: a method wherein dimethyl acetal derived from the sn-1 position of plasmalogen are analyzed and regarded as CP amount, and a method wherein phospholipids in a sample are fractionated into phospholipid classes by TLC, and molecular species are analyzed by gas chromatography. Recently, however, a method using liquid chromatography is widely used, because this method allows many samples to be quickly analyzed with high sensitivity. In the present invention, liquid chromatography (HPLC) can be used. Further, a method for analyzing molecular species of plasmalogen using mass spectrometry is also known. In the present invention, the mass spectrometer can be used. These methods will now be explained in detail.

(Measurement of Total CP Amount by HPLC)

As a method for quantifying total CP amount in a sample to be tested (such as serum or plasma) using HPLC, the following method is preferable. Firstly, cAP as the internal standard is added to the sample and lipids are extracted, or cAP as the internal standard is added to the extracted lipids. Then, the whole is reacted with radioactive iodine reagent in methanol, and an obtained radioactive iodine-bound CP is eluted by HPLC and the radioactivity thereof is measured.

The radioactive iodine reagent can be prepared as follows. Commercially available radioactive iodine ($Na^{125}I$) is oxidized using an oxidizing agent such as hydrogen peroxide over night at room temperature, under acidic conditions of pH5.5 to 6.0 in methanol. 70% or more of the resulting reagent is radioactive triiodide ($I^{3-}$) which can specifically bind to plasmalogen.

The reaction between the extracted lipids from the sample to be tested and radioactive iodine reagent is performed as follows. Sample dissolved in methanol containing CP (for example, 0.001 to 0.1 mL of sample extracted from serum, which is estimated to contain 0.1 to 400 nmol of CP) and radioactive iodine reagent (for example, 0.001 to 0.1 mL of reagent containing 10 mM iodine atom) are mixed, and allowed to stand at a predetermined temperature, in general between 4° C. and 30° C., for a predetermined period of time, in general, for between 12 hours and 24 hours.

The elution of lipids by HPLC is performed as follows. Lipids may be eluted by using a column capable of distinguishing choline glycerophospholipid, ethanolamine glycerophospholipid, and the internal standard material (for example, a Diol column, and an appropriate elution solvent (for example, acetonitrile/water/acetic acid/ammonia).

CP (strictly, an iodine-bound choline glycerophospholipid derived from CP) can be detected by measuring radioactivity by a gamma counter, preferably a flow-type gamma counter.

The internal standard material used together with radioactive iodine reagent is not limited, so long as it can stoichiometrically bind to iodine and it is fat-soluble compound, but includes, for example, vinyl ether compounds such as 2-Hydroxyethyl vinyl ether or diethylene glycol divinyl ether; lysoplasmalogen or serine plasmalogen which hardly exist in a living body; the above synthetic choline plasmalogen which does not exist in a living body, in particular choline plasmalogen wherein $R^3$ is an alkyl group having 4 to 6 or 22 to 24 carbon atoms; and 1-alkenyl cyclic phosphatidic acid. Preferably, 1-alkenyl cyclic phosphatidic acid (cAP) may be used. This is because the physicochemical characteristics of cAP are similar to those of choline glycerophospholipid. Further, cAP can be easily separated by HPLC, and has highly preservation stability.

(Measurement of Total CP Amount by Mass Spectrometry)

A method for analyzing total CP amount using mass spectrometry can perform in accordance with the method for measuring molecular species of CP as described below. The method of extraction of plasmalogen from the sample to be tested, internal standard material, and mass spectrometer are not particularly limited. Concentrations of the main 30 types of plasmalogens presented in a living body can be measured by the method for measuring molecular species of CP described below. Therefore, the total CP amount in the sample to be tested can be calculated by adding together obtained the concentrations of molecular species of CP.

<<Method for Measuring Molecular Species of CP>>

The method for measuring molecular species of CP is not particularly limited, so long as molecular species of CP can be measured separately, but includes, for example, the method using gas chromatography, the method using high-performance liquid chromatography, and the mass spectrometry method. In particular, the mass spectrometry method is preferable. The mass spectrometry method is not particularly limited, but includes, for example, a method using high-performance liquid chromatography (HPLC) (hereinafter referred to as a LC/MS method), a method using gas chromatography (GC) (hereinafter referred to as a GC/MS method), and a method using capillary electrophoresis (CE) (hereinafter referred to as a CE-MS method). Specifically, a method of liquid chromatography-tandem mass spectrometry (hereinafter referred to as a LC-MS/MS method) which is one of the LC/MS methods may be used. This is because the sensitivity of the LC/MS method is high, and further various molecular species of plasmalogen can be analyzed according to the LC/MS method.

The method for extracting plasmalogen from the sample to be tested is not particularly limited, and thus the aforementioned extraction method can be used. However, the preferable extraction method is the method wherein a sample is freeze dried and extracted using chloroform/methanol mixed solvent. The internal standard material is not limited, so long as all calibration curves of each molecular species of CP can be made using the internal standard material. But the synthetic choline plasmalogen is preferable, because it has a structure similar to CP. The method of preparation of the synthetic choline plasmalogen is not limited, but the synthetic choline plasmalogen can be prepared by the chemical synthetic procedure or the enzymatic synthesis procedure. Types of the synthetic choline plasmalogen is not particularly limited, so long as it does not exist in a living body, For example, the choline plasmalogen of above formula (3) which has tricosanoic acid at the sn-1 position and oleic acid at the sn-2 position (hereinafter sometimes referred to as a p23:0/18:1).

The synthetic choline plasmalogen may be added to the sample to be tested before or after extracting plasmalogen. However, preferably, the synthetic choline plasmalogen is added to the sample to be tested before extracting plasmalogen, because it is possible to correct for the extraction efficiency of plasmalogen.

In the mass spectrometry method for measuring plasmalogen, the correction method using the internal standard compound is not particularly limited, but a correction method wherein a calibration curve is prepared from serially-diluted and known concentrations of plasmalogen and serially-diluted and known concentrations of the internal standard compound, can be preferably used. That is, the calibration curve can be prepared using standard samples wherein internal standard compound is added to the standard solutions containing plasmalogen of various concentrations.

When the calibration curve is prepared in the mass spectrometry method by LC-MS/MS method, the ratio of the area of the fragment peak of the internal standard compound and the area of the fragment peak of plasmalogen are measured. Then, a high-integrity calibration curve can be prepared by plotting the resulting ratios on a graph. In the measurement of the sample to be tested, the internal standard compound is added at known concentration to the sample derived from a living body, and plasmalogens and the internal standard compound are measured. Then, an accurate measurement value can be obtained by applying the resulting ratio of the area of the fragment peak of the internal standard compound and the area of the fragment peak of plasmalogen, to the calibration curve.

It is known that when a plasmalogen is analyzed by mass spectrometry, some fragments are produced from plasmalogen. A fragment for preparing calibration curve is not to particularly limited, but, a fragment of the general formula (5):

[Chem. 7]

(5)

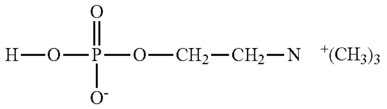

derived from choline phosphoric acid (hereinafter referred to as a choline phosphoric acid fragment) is preferably used as a fragment peak of the synthetic choline plasmalogen and plasmalogen in the sample. That is, the calibration curve can be prepared by plotting ratios of the area of choline phosphoric acid of the synthetic choline plasmalogen and the area of choline phosphoric acid of plasmalogen in the sample.

Each concentration of molecular species of plasmalogen can be measured by using the prepared calibration curve. In the main molecular species of choline plasmalogens in the sample to be tested, there are three types of molecules at the sn-1 position, i.e. 16:0, 18:0, or 18:1, and ten types of molecules at the sn-2 position i.e. 16:0, 18:0, 18:1, 18:2, 18:3, 20:4, 20:5, 22:4, 22:5, or 22:6. Thus, there are thirty types of main molecular species of choline plasmalogens in a living body. In connection to this, molecules at the sn-1 position and molecules at the sn-2 position of ethanolamine plasmalogens are the same as those of choline plasmalogens. Therefore, there are also thirty types of main molecular species of ethanolamine plasmalogens in a living body. Accordingly, the total CP amount can be calculated by adding together all the concentrations of molecular species of choline plasmalogens in the sample.

The term "side chain at the sn-1 position" as used herein means "—CH═CH—$R^1$" of plasmalogen. Regarding the number of carbon atoms and the number of double bond contained in the side chain, the description "16:1", for example, means that the number of carbon atoms is 16 and the number of double bonds, except for vinyl ether bonds, is 1. Further, the term "side chain at the sn-2 position" as used herein means "—CO—$R^2$" of plasmalogen. Regarding the number of carbon atoms and the number of double bond contained in the side chain, the description "20:4", for example, means that the number of carbon atoms is 24 and the number of double bonds is 4.

<<Detection of Metabolic Syndrome or Life-Style Related Disease Using Total CP Amount>>

As described in the Examples, the measurement values of total CP amount obtained by the method for measuring total CP amount are highly correlated to body weight (correlation coefficient: −0.334), waist circumference (correlation coefficient: −0.375), triglyceride (correlation coefficient: −0.327), HDL-C (correlation coefficient: 0.714), sdLDL (correlation coefficient: −0.224), AIP (correlation coefficient: −0.576), and adiponectin (correlation coefficient: 0.314) (Table 3 and Table 4).

Further, the total CP amount of the normal human group is 65.9 μM, whereas the total CP amount of metabolic syndrome group is 56.5 μM. That is, in the metabolic syndrome group, the total CP amount is significantly lower (Table 5).

<<Detection of Metabolic Syndrome or Life-Style Related Disease Using Concentrations of Molecular Species of CP>>

In the detection method of the present invention, concentrations of each CP molecular species, rather than the total CP amount, can be used for detecting metabolic syndrome or life-style related disease. For example, in accordance with the differences of side chains at the sn-1 position and the sn-2 position, the concentration of each of the thirty types of CP molecular species may be used for detection. Further, the concentration of each of the three types of CP molecular species may be used for detection according to the differences of side chains at the sn-1 position, and the concentration of each of the ten types of CP molecular species may be used for detection according to the differences of side chains at the sn-2 position. However, the concentration of choline plasmalogen having oleic acid at the sn-2 position (hereinafter sometimes referred to as a C18:1 CP), or a concentration of choline plasmalogen having linoleic acid at the sn-2 position (hereinafter sometimes referred to as a C18:2 CP) is preferable, and particularly the concentration of C18:1 CP is more preferable.

As described in the Examples, the measurement values of C18:1 CP are highly correlated to body weight (correlation coefficient: −0.438), waist circumference (correlation coefficient: −0.461), triglyceride (correlation coefficient: −0.415), HDL-C (correlation coefficient: 0.757), sdLDL (correlation coefficient: −0.319), AIP (correlation coefficient: −0.641), and adiponectin (correlation coefficient: 0.446)(Table 4). Further, the concentration of C18:1 CP in the normal human group is 6.3 μM, whereas the total CP amount in the metabolic syndrome group is 4.8 μM. That is, in the metabolic syndrome group, the concentration of C18:1 CP is significantly low (Table 5).

<<Detection of Metabolic Syndrome or Life-Style Related Disease Using a Ratio of CP Concentration and Phospholipid Concentration>>

According to another embodiment of the detection method of the present invention, metabolic syndrome or life-style related disease can be detected using the ratio of the measurement value of choline plasmalogen concentration and the measurement value of phospholipid concentration in the sample to be tested. As the choline plasmalogen concentration, the total CP amount or the concentration of a particular CP molecular species can be used, but a concentration of C18:1 CP or C18:2 CP is preferably used.

Further, the calculating formula for the ratio of the measurement value of choline plasmalogen concentration and the measurement value of phospholipid concentration in sample to be tested, is not particularly limited. For example, the ratio may be calculated by the formula "CP concentration/phospholipid concentration". In the above formula, the calculated value means the concentration of total choline plasmalogen with respect to phospholipid concentration, or the concentration of molecular species of CP with respect to phospholipid concentration.

A measurement of total phospholipid amount in the sample to be tested may be carried out in accordance with conventional methods. For example, there may be mentioned: a method wherein phosphorus amount produced by an asking treatment of extracted lipid is measured using phosphomolybdic acid reaction, or the like; HPLC method; or choline oxidase DADS method (for example, Phospholipid C-test WAKO: WAKO Chemicals).

<<Detection of Metabolic Syndrome or Life-Style Related Disease Using Ratio of CP Concentration and Body Weight of Subject>>

According to another embodiment of the detection method of the present invention, metabolic syndrome or life-style related disease can be detected using the ratio of the measurement value of choline plasmalogen concentration and the measurement value of body weight of a subject. As the choline plasmalogen concentration, the total CP amount or the concentration of a particular CP molecular species can be used, but a concentration of C18:1 CP or C18:2 CP is preferably used.

Further, the calculating formula for the ratio of the measurement value of choline plasmalogen concentration and the measurement value of body weight of the subject, is not particularly limited. For example, the ratio may be calculated by the formula "CP concentration/body weight of subject (kg)". The value obtained by the above formula means the concentration of choline plasmalogen with respect to 1 kg of body weight. Measurement of the body weight of the subject may be carried out in accordance with conventional method.

<<Detection of Metabolic Syndrome or Life-Style Related Disease Using Ratio of CP Concentration and Triglyceride Concentration>>

According to another embodiment of the detection method of the present invention, metabolic syndrome or life-style related disease can be detected using the ratio of CP concentration and triglyceride concentration in a sample to be tested. As the choline plasmalogen concentration, the total CP amount or the concentration of a particular CP molecular species can be used, but a concentration of C18:1 CP or C18:2 CP is preferably used.

Further, the calculating formula for the ratio of the measurement value of choline plasmalogen concentration and the measurement value of triglyceride concentration, is not particularly limited. For example, the ratio may be calculated by the formula "CP concentration/triglyceride concentration". Measurement of the triglyceride concentration in the sample to be tested may be carried out in accordance with a conventional method.

Each ratio of: the CP concentration to phospholipid concentration, the ratio of CP concentration to body weight of the subject, the ratio of CP concentration to triglyceride concentration, is highly correlated to body weight, waist circumference, triglyceride, HDL-C, sdLDL, AIP, and adiponectin (Table 3 and Table 4). That is, the above ratios are significantly different between the normal human group and the metabolic syndrome group. In particular, the differences between the normal human group and the metabolic syndrome group in order of decreasing significance are: the ratio of CP concentration to triglyceride concentration, the ratio of CP concentration to body weight of the subject, and the ratio of CP concentration to phospholipid concentration.

In the detection method of the present invention, the concentration of choline plasmalogen or the concentration of molecular species of choline plasmalogen in the sample to be tested are measured. Then, the resulting measurement value is compared to the reference value which is established from measurement values of choline plasmalogen concentrations in the samples of normal humans, so that metabolic syndrome or life-style related disease can be detected.
The reference value of normal humans and the cut-off point for detecting metabolic syndrome or life-style related disease are determined by a controlled clinical trial.

The detection method of the present invention can be used for preventing a development of metabolic syndrome or life-style related disease, or monitoring the effect of treatment. Further, the detection method of the present invention can be used as a biomarker of risk or degree of seriousness of metabolic syndrome or life-style related disease. In particular, high measurement values of triglyceride, sdLDL, and AIP indicate the risk of development of arteriosclerosis, and low measurement values of HDL-C and adiponectin also indicate the risk of development of arteriosclerosis. The concentration of choline plasmalogen, the concentration of molecular species of choline plasmalogen, the ratio of CP concentration and phospholipid concentration, the ratio of CP concentration and body weight of the subject, and the ratio of CP concentration and triglyceride concentration, obtained by the detection method of the present invention, are highly correlated to triglyceride, HDL-C, sdLDL, adiponectin, and AIP, and thus, can be used for preventing the development of arteriosclerosis or as a risk marker of arteriosclerosis.

<<Life-Style Related Disease>>

The life-style related disease detected by the method of the present invention, is not limited, so long as it is a disease mainly caused by food, a sleeping, or articles such as cigarettes or alcohol. There may be mentioned, for example, diabetes, dyslipidemia (hyperlipemia), hypertension, obesity, cancer, stroke, arteriosclerosis, cardiomyopathy, cardiac infarction, arrhythmia, fatty liver, alcohol liver disease, gastric ulcer, duodenal ulcer, cholecystolithiasis, periodontics, draft, hyperuricemia, and osteoporosis. According to the detection method of the present invention, dyslipidemia, hypertension, and arteriosclerosis can be detected at high rates.

<<Metabolic Syndrome>>

The term "metabolic syndrome" as used herein means a symptom wherein waist circumference of the subject is 85 cm or more in man, or 90 cm or more in woman, which is "caution should be exercised"; and the subject has two of the following three items: (1) serum lipid abnormality (i.e. 150 mg/dL or more of triglyceride value), (2) high-blood pressure (130 mmHg or more of systolic blood pressure, and 85 mmHg or more of diastolic blood pressure), (3) elevated blood glucose (110 mg/dL or more of fasting blood glucose level).

[2] Kit for Detecting Metabolic Syndrome or Life-Style Related Disease

The kit for detecting metabolic syndrome or life-style related disease of the present invention comprises a 1-alkenyl cyclic phosphatidic acid of the general formula (1):

[Chem. 8]

(1)

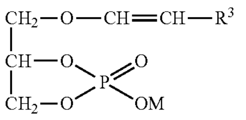

wherein $R^3$ is an alkyl group having 4 to 26 carbon atoms or an alkenyl group having 4 to 26 carbon atoms, and M is a hydrogen atom or a counter cation, as an internal standard material for analyzing plasmalogen, or a compound of the general formula (2):

[Chem. 9]

(2)

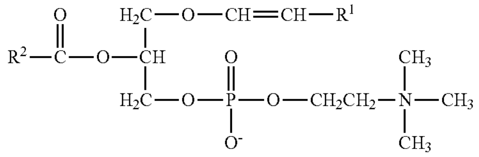

wherein $R^1$ is an alkyl group having 7, 9, 11, 13, 15, 17, 19, or 21 carbon atoms, and $R^2$ is an alkyl group having 8 to 21 carbon atoms or an alkenyl group having 8 to 21 carbon atoms, as an internal standard material for analyzing plasmalogen.

The kit for detecting metabolic syndrome or life-style related disease of the present invention can be used for the method of detecting metabolic syndrome or life-style related disease of the present invention. Therefore, the kit may contain an extraction agent for extracting plasmalogen from a sample to be tested. Examples of the extraction agent include: an extraction agent for Bligh & Dyer method, an extraction agent for Folch method, a hexane/ethanol mixed solvent, an ether/ethanol mixed solvent, or a chloroform/methanol mixed solvent. Further, the kit of the present invention may contain a manual that describes its use for detection of metabolic syndrome or life-style related disease. In addition, these descriptions may also be attached to the container of the kit. Furthermore, the detection kit of the present invention can be used for diagnosis of metabolic syndrome or life-style related disease.

EXAMPLES

The present invention will now be further illustrated by, but is by no means limited to, the following Examples.

Example 1

Sera isolated from bloods of 451 subjects aged between 21 and 66 (382 men, 69 women, average age: 39.6, 216 subjects aged 40 years or older) were prepared. Lipid was extracted from the serum and the amount of CP (hereafter referred to as the CP amount) was quantified. Further, the concentration of phospholipid in serum was measured using a kit "Phospholipid C-test WAKO".

Quantification of the CP amount was carried out by the following measuring method using HPLC.

Extraction of total lipids from blood was carried out according to the following procedure. 0.12 mL of ether and 0.36 mL of ethanol were added to 0.15 mL of serum obtained by centrifuging blood, and they were mixed for 10 minutes. Further, 0.9 mL of 2M sodium chloride solution, and 0.48 mL of ether were added to the mixture, and they were mixed for 5 minutes. The mixture was centrifuged at 3000 rpm for 15 minutes and the upper layer collected. Further, 0.3 mL of ether was added to the lower layer and they were mixed for 5 minutes. This mixture was further centrifuged at 3000 rpm for 15 minutes to collect a new upper layer. The two collected upper layers were mixed and the solvents were removed by spraying with nitrogen gas. Then, the total lipids extracted were dissolved in 0.1 mL of methanol containing 0.1 mM internal standard material (cAP).

The cAP, which is the internal standard material, was prepared according to the following procedure. About 5 mg of lyso-choline plasmalogen (Funakoshi) which is dissolved in chloroform was poured into a 50 mL-volume screw-top test tube. The chloroform was evaporated by spraying with nitrogen gas, to obtain a solid body. Immediately, 1.5 mL of ether, 1.5 mL of 100 mM sodium acetate-40 mM calcium chloride buffer (pH5.6) and 10 U of phospholipase D were added thereto, and the mixture was incubated at 40° C. in a hot-water bath, while shaking. After reacting for about 3 hours, it was confirmed by thin layer chromatography (TLC) that most lyso plasmalogen had been disappeared. The ether was evaporated from the reaction liquid by spraying with nitrogen gas. Then, 1.2 mL of ether and 3.6 mL of ethanol were added to the resulting solid body, and they were mixed for 10 minutes. Further, 9.0 mL of 2M sodium chloride solution and 4.8 mL of ether were added to the mixture and it was further mixed for 5 minutes. The mixture was centrifuged at 3000 rpm for 15 minutes and the upper layer collected. 0.3 mL of ether was added to a lower layer and they were mixed for 5 minutes. The mixture was centrifuged at 3000 rpm for 15 minutes and the upper layer collected. The two collected upper layers were mixed and the solvents were removed by spraying with nitrogen gas. Then, the obtained solid body was dissolved in an appropriate volume of methanol, to be 0.1 mM of cAP solution.

The reagent containing triiodide ion ($I^{3-}$) was prepared according to the following procedure. A commercially available radioactive iodine ($Na^{125}I$, 37 MBq/0.01 mL), 1 mL of 50 mM sodium hydroxide-20 mM potassium iodide-methanol solution, 0.3 mL of 2.0M acetic acid-methanol solution, 0.6 mL of 1.0M hydrogen peroxide-methanol solution and 0.1 mL of methanol were mixed, and allowed to stand overnight at room temperature. The resulting mixture was kept at room temperature and used as a 10 mM radioactive iodine reagent.

0.04 mL of each extracted serum lipid sample and 0.01 mL of 10 mM radioactive iodine reagent were mixed and incubated at 4° C. for 16 hours. HPLC was applied to 0.02 mL of the reaction sample containing 1.74 nmole of cAP as the internal standard in accordance with the following conditions. As an eluting buffer, acetonitrile/water/acetic acid/ammonia (93:6.895:0.07:0.035) was used, and an isocratic elution was carried out at a flow rate of 1 ml/min. As a column, Lichrospher 100 Diol 250-4(Merck) was used. The measurement time was 15 minutes or more. As a detector, flow type γ counter (BIOSCAN) was used.

Data were analyzed using SMARTCHROM (KYA Technologies), to quantify the CP amount using the predetermined calibration curve prepared from peak areas of CP and cAP. Iodine molecules specifically bind to a vinyl ether bond of plasmalogen in methanol, and thus a measured value can be obtained by the decrease in the absorbance of iodine molecule due to the reaction with plasmalogen. The calibration curve was prepared using the measured value and peak area obtained by SMARTCHROM.

Firstly, the effect of use of the internal standard was validated by 4 quantitative tests. An extracted serum sample was obtained in accordance with the above method of extraction of total lipids, except that 0.02 mL of serum was used instead of 0.015 mL of serum. Subsequently, the extracted sample was reacted with the radioactive iodine reagent, and HPLC was applied to the resulting reaction sample. Then, a correction coefficient (i.e. (A)/(B)) was calculated from the added cAP amount contained in 0.02 mL of reaction sample (A) and a measured cAP amount (B). The measured CP amount was multiplied by the correction coefficient to calculate a corrected CP amount. Standard deviations and variation coefficients of the 4 quantitative tests are shown in Table 1. Further, in cases wherein the internal standard was not used, i.e. when the correction coefficient was not used, standard deviations and variation coefficients of the 4 quantitative tests are also shown in Table 1. Furthermore, EP amounts were also measured in accordance with a similar procedure and the results are shown in Table 1.

TABLE 1

| | Additive amount of cAP 1.74 nmol (A) | | CP value | | EP value | |
|---|---|---|---|---|---|---|
| | cAP value (B) nmol | correction coefficient = (A)/(B) | Without correction nmol | Correction by internal std. nmol | Without correction nmol | Correction by internal std. nmol |
| Measurement 1 | 1.71 | 1.02 | 1.33 | 1.36 | 2.04 | 2.08 |
| Measurement 2 | 1.54 | 1.13 | 1.25 | 1.41 | 1.84 | 2.08 |
| Measurement 3 | 1.67 | 1.04 | 1.27 | 1.33 | 1.92 | 2.00 |
| Measurement 4 | 1.45 | 1.20 | 1.16 | 1.39 | 1.63 | 1.95 |
| Mean | 1.59 | — | 1.25 | 1.37 | 1.86 | 2.03 |
| standard deviation | 0.12 | — | 0.071 | 0.038 | 0.17 | 0.06 |
| variation coefficient % | 7.39 | — | 5.65 | 2.78 | 9.22 | 3.08 |

As shown in Table 1, the standard deviations and variation coefficients of the measurement values obtained using cAP as the internal standard were significantly lower, compared to those obtained not using cAP. That is, as a method for measuring plasmalogen in serum, this method is, superior.

Therefore, the cAP was used as the internal standard in the following measurements of the CP amount.

Example 2

In this Example, molecular species of choline plasmalogen in sera of the 451 subjects aged between 21 and 66 (382 men, 69 women, average age: 39.6, and 216 of the subjects were aged 40 years or more) of Example 1, were measured using LC-MS/MS.

An extraction of total lipids from blood was carried out in accordance with the following procedure. 0.15 mL of serum obtained by centrifuging blood, was lyophilized, and then 0.5 mL of a mixture of chloroform and methanol (2:1) containing 50 pmol of synthetic choline plasmalogen having tricosanoic acid at the sn-1 position and oleic acid at the sn-2 position as the internal standard (p23:0/18:1), was added. The whole was mixed for 10 minutes, and allowed to stand at a room temperature for 30 minutes. The mixture was centrifuged at 3000 rpm for 15 minutes and the upper layer collected. Further, 1 mL of mixture of chloroform and methanol (2:1) was added to the lower layer, and they were mixed and allowed to stand. The mixture was centrifuged and the upper layer collected. The two collected upper layers were mixed and the solvents were removed by spraying with nitrogen gas. Then the obtained solid body was dissolved in 1 mL of methanol and the resulting solution was filtrated with a filter. The solution was appropriately diluted with methanol, and analyzed using LC-MS/MS.

A measurement condition for LC-MS/MS is as follows.

<Conditions of LC (High-Performance Liquid Chromatography)>

LC system: Accela UHPLC System

Eluent A: 5 mM ammonium formate solution

Eluent B: acetonitrile

Column: Waters ACQUITY UPLC BEH C8 (2.1×100 mm, 1.7 μm)

Temperature of column: 60° C.

Flow rate: 0.6 mL/min

Condition of UHPLC eluent is shown in Table 2.

TABLE 2

| Time (min) | Eluent A (%) | Eluent B (%) |
|---|---|---|
| 0 | 80 | 20 |
| 1 | 40 | 60 |
| 1.5 | 20 | 80 |
| 9 | 15 | 85 |
| 11 | 10 | 90 |
| 12.2 | 5 | 95 |
| 14.8 | 5 | 95 |
| 15 | 80 | 20 |

<Conditions for MS/MS (Tandem Mass Spectrometry)>

MS system: TSQ Quantum system

Ionization mode: Heated ESI, positive

Capillary voltage: 3.2 kV

Corn voltage: 35V

Desolvation temperature: 400° C.

Source temperature: 80° C.

Collision energy: 32 eV (choline plasmalogen)

A calibration curve for quantifying choline plasmalogen in a sample to be tested was prepared as follows. A synthetic choline plasmalogen (p16:0/20:4) was dissolved in methanol to prepare a standard stock solution (1.7 μmol/mL). The standard stock solution was diluted with methanol to prepare four concentration standard solutions, i.e. standard solutions of 0.085 pmol, 0.17 pmol, 0.34 pmol, and 0.51 pmol. Next, 100 pmol of synthetic choline plasmalogen (p23:0/18:1) was added to each standard solution. Each standard solution is analyzed in accordance with the above measurement conditions for LC-MS/MS. The peak area ratio of choline phosphoric acid fragment of p16:0/20:4 and choline phosphoric acid fragment of p23:0/18:1 in each standard solution was calculated to prepare a calibration curve. Choline plasmalogen in human plasma samples was quantified using the calibration curve.

Average values and standard deviations of measured amounts of choline plasmalogen in serum samples, using: the method wherein the synthetic choline plasmalogen having tricosanoic acid at the sn-1 position and oleic acid at the sn-2 position (p23:0/18:1) was used as the internal standard, the method wherein cholic acid was used as the internal standard, and the external standard method, were compared. As a result, when the synthetic choline plasmalogen having tricosanoic acid at the sn-1 position and oleic acid at the sn-2 position (p23:0/18:1) was used as the internal standard, a corrected measurement value is high and a variation (standard deviation) is low, compared to the external standard method and the method wherein cholic acid was used as the internal standard. That is to say, the measurement value corrected by using the plasmalogen as the internal standard was highly accurate.

There are three types of molecule that can be at the sn-1 position of plasmalogen i.e. 16:0, 18:0, or 18:1, and there are ten types of molecule that can be at the sn-2 position of plasmalogen i.e. 16:0, 18:0, 18:1, 18:2, 18:3, 20:4, 20:5, 22:4, 22:5, or 22:6. Thus, there are thirty types of measured molecular species of choline plasmalogens. From among these thirty molecular species, analysis data of the plasmalogen having oleic acid at the sn-2 position (18:1), and the plasmalogen having linoleic acid at the sn-2 position (18:2), are shown in Table 4.

Example 3

The above 451 subjects were examined for the following clinical test items; age, sex, body height, body weight, BMI, waist circumference, blood pressure, GOT, GPT, γ-GTP, uric acid, triglyceride, HDL-C, LDL-C, blood glucose level, adiponectin, sdLDL, hsCRP, AIP, or the like. Then, correlations between serum plasmalogen amount, CP amount, EP amount, CP/PL (phospholipid), CP/body weight, CP/triglyceride, or CP/EP; and the above clinical test items, were analyzed.

Of the above correlations, the correlations between body weight, waist circumference, triglyceride, HDL-C, sdLDL, adiponectin, or AIP; and CP amount, CP/PL, CP/body weight, CP/triglyceride, CP/EP, are shown in Table 3.

TABLE 3

| | Body weight | Waist circumference | Triglyceride | HDL-C | sdLDL | AIP | Adiponectin |
|---|---|---|---|---|---|---|---|
| Total CP amount | −0.334 | −0.375 | −0.327 | 0.714 | −0.224 | −0.576 | 0.314 |
| CP/PL | −0.374 | −0.408 | −0.542 | 0.506 | −0.458 | −0.675 | 0.319 |
| CP/Body weight | — | −0.672 | −0.398 | 0.732 | −0.347 | −0.631 | 0.413 |
| CP/Triglyceride | −0.406 | −0.452 | — | 0.676 | −0.544 | — | 0.358 |
| CP/EP | −0.185 | −0.196 | −0.265 | 0.167 | −0.242 | −0.241 | 0.172 |

Further, the correlations between body weight, waist circumference, triglyceride, HDL-C, sdLDL, adiponectin, or AIP; and CP amount, C18:1 CP, C18:1 CP/PL, C18:1 CP/triglyceride, C18:1 CP/body weight, C18:2 CP, C18:2 CP/PL, C18:2 CP/triglyceride, C18:2 CP/body weight, or CP/EP, are shown in Table 4.

TABLE 4

| | Body weight | Waist circumference | HDL-C | HDL-C | sdLDL | AIP | Adiponectin |
|---|---|---|---|---|---|---|---|
| Total CP amount | −0.334 | −0.375 | −0.327 | 0.714 | −0.224 | −0.576 | 0.314 |
| C18:1CP | −0.438 | −0.461 | −0.415 | 0.757 | −0.319 | −0.641 | 0.446 |
| C18:1CP/PL | −0.463 | −0.479 | −0.572 | 0.593 | −0.5 | −0.715 | 0.453 |
| C18:1CP/Triglyceride | −0.443 | −0.477 | — | 0.702 | −0.544 | — | 0.408 |
| C18:1CP/Body weight | — | −0.666 | −0.426 | 0.731 | −0.385 | −0.641 | 0.474 |
| C18:2CP | −0.334 | −0.407 | −0.339 | 0.651 | −0.265 | −0.562 | 0.371 |
| C18:2CP/PL | −0.361 | −0.423 | −0.508 | 0.475 | −0.444 | −0.634 | 0.365 |
| C18:2CP/Trigiycende | −0.454 | −0.496 | — | 0.588 | −0.492 | — | 0.391 |
| C18:2CP/Body weight | — | −0.611 | −0.345 | 0.600 | −0.371 | −0.553 | 0.435 |
| CP/EP | −0.185 | −0.196 | −0.265 | 0.167 | −0.242 | −0.172 | 0.241 |

As a result, the CP amount was highly correlated to some of the clinical test items which are risk factors of arteriosclerosis. For example, the correlation coefficient between CP amount and body weight was −0.334, the correlation coefficient between CP amount and waist circumference was −0.375, the correlation coefficient between the CP amount and triglyceride was −0.327, the correlation coefficient between CP amount and HDL-C was 0.714, the correlation coefficient between the CP amount and sdLDL was −0.224, the correlation coefficient between the CP amount and AIP was −0.576, and a correlation coefficient between the CP amount and adiponectin was 0.314.

Further, it was found that the ratio of total phospholipid amount to the total CP amount (hereinafter referred to as a "CP/PL ratio") was more strongly correlated to these factors, than the total CP amount was. For example, the correlation coefficient between CP/PL ratio and body weight was −0.374, the correlation coefficient between CP/PL ratio and waist circumference was −0.408, the correlation coefficient between CP/PL ratio and triglyceride was −0.542, the correlation coefficient between CP/PL ratio and sdLDL was −0.458, the correlation coefficient between CP/PL ratio and AIP was −0.674, and the correlation coefficient between CP/PL ratio and adiponectin was −0.319.

It was found that ratios of the total CP amount, to body weight or triglyceride, which are certainly contained in general clinical test items, were more strongly correlated to these factors, than the total CP amount was. For example, the correlation coefficient between CP/body weight ratio and waist circumference was −0.672, the correlation coefficient between CP/body weight ratio and triglyceride was −0.398, the correlation coefficient between CP/body weight ratio and HDL-C was 0.732, the correlation coefficient between CP/body weight ratio and sdLDL was −0.347, the correlation coefficient between CP/body weight ratio and AIP was −0.631, and the correlation coefficient between CP/body weight ratio and adiponectin was 0.413. The correlation coefficient between CP/triglyceride ratio and body weight was −0.406, the correlation coefficient between CP/triglyceride ratio and waist circumference was −0.452, the correlation coefficient between CP/triglyceride ratio and sdLDL was −0.544, and the correlation coefficient between CP/triglyceride and adiponectin was 0.358.

Next, as a result of a analysis of CP molecular species, the amount of choline plasmalogen having oleic acid at the sn-2 position (hereinafter referred to as "C18:1 CP amount") or the amount of choline plasmalogen having linoleic acid at the sn-2 position (hereinafter referred to as "C18:2 CP amount") was more strongly correlated to arteriosclerosis-related factors and metabolic syndrome-related factors, than the total CP amount was. For example, the correlation coefficient between C18:1 CP amount and body weight was −0.438, the correlation coefficient between C18:1 CP amount and waist circumference was −0.461, the correlation coefficient between C18:1 CP amount and HDL-C was 0.757, the correlation coefficient between C18:1 CP amount and triglyceride was −0.415, the correlation coefficient between C18:1 CP amount and sdLDL was −0.319, the correlation coefficient between C18:1 CP amount and adiponectin was 0.446, and the correlation coefficient between C18:1 CP amount and AIP was −0.641.

Further, it was found that the ratio of the total amount of phospholipid to the CP18:1 amount (hereinafter referred to as a "CP18:1/PL") was more strongly correlated to these factors, than the total CP amount was. For example, the correlation coefficient between CP18:1/PL and body weight was −0.463, the correlation coefficient between CP18:1/PL and waist circumference was −0.479, the correlation coefficient between CP18:1/PL and triglyceride was −0.572, the correlation coefficient between CP18:1/PL and sdLDL was −0.500, the correlation coefficient between CP18:1/PL and adiponectin was 0.453, and the correlation coefficient between CP18:1/PL and AIP was 0.715.

It was found that the ratios of the total CP18:1 amount, to body weight or triglyceride, which are certainly contained in general clinical test items, were more strongly correlated to arteriosclerosis-related factors and metabolic syndrome-related factors, than the total CP amount was. For example, the correlation coefficient between CP18:1/triglyceride ratio and waist circumference was −0.477, the correlation coefficient between CP18:1/triglyceride ratio and sdLDL was −0.544, the correlation coefficient between CP18:1/triglyceride ratio and body weight was −0.443, and the correlation coefficient between CP18:1/triglyceride ratio and adiponectin was 0.408. Further, the correlation coefficient between CP18:1/body weight ratio and HDL-C was 0.731, the correlation coefficient between CP18:1/body weight ratio and waist circumference was 0.666, the correlation coefficient between CP18:1/body weight ratio and AIP was −0.641, and the correlation coefficient between CP18:1/body weight ratio and adiponectin was 0.474. These correlation coefficients were far higher than those of total CP amount.

Further, correlation coefficients between total CP18:2 amount and the above factors were equal to those of C18:1 CP. For example, the correlation coefficient between C18:2 CP amount and body weight was −0.334, the correlation coefficient between C18:2 CP amount and waist circumference was −0.407, the correlation coefficient between C18:2 CP amount and HDL-C was 0.651, the correlation coefficient between C18:2 CP amount and triglyceride was −0.339, the correlation coefficient between C18:2 CP amount and sdLDL was −0.265, the correlation coefficient between C18:2 CP amount and adiponectin was 0.371, and the correlation coefficient between C18:2 CP amount and AIP was −0.562.

It was found that the CP18:2/PL ratio was more strongly correlated to these factors, than the total CP18:2 amount was. For example, the correlation coefficient between C18:2 CP/PL ratio and body weight was −0.361, the correlation coefficient between C18:2 CP/PL ratio and waist circumference was −0.423, the correlation coefficient between C18:2 CP/PL ratio and triglyceride was −0.508, the correlation coefficient between C18:2 CP/PL ratio and sdLDL was −0.444, and the correlation coefficient between C18:2 CP/PL ratio and AIP was −0.634.

It was found that ratios of total CP18:2 amount, to body weight or triglyceride, which are certainly contained in general clinical test items, were more strongly correlated to arteriosclerosis-related factors and metabolic syndrome-related factors, than the total CP amount was. For example, the correlation coefficient between CP18:2/triglyceride ratio and waist circumference was −0.496, the correlation coefficient between CP18:2/triglyceride ratio and sdLDL was −0.492, the correlation coefficient between CP18:2/triglyceride ratio and body weight was −0.454, the correlation coefficient between CP18:2/triglyceride ratio and adiponectin was 0.391. Further, the correlation coefficient between CP18:2/body weight ratio and waist circumference was −0.611, and the correlation coefficient between CP18:2/body weight ratio and adiponectin was 0.435. These correlation coefficients were far higher than those related to the total CP amount.

Example 4

From among the 451 subjects in Example 1, 156 subjects which were 40 years or more of age, and persons subject to health checks for metabolic syndrome, were classified into three groups in accordance with diagnosis criterion of metabolic syndrome.

That is, a person wherein waist circumference is 85 cm or more in man, or 90 cm or more in woman, is "caution should be exercised"; and subjects having two from among the following three items; (1) serum lipid abnormality (i.e. 150 mg/dL or more of triglyceride value), (2) high-blood pressure (130 mmHg or more of systolic blood pressure, and 85 mmHg or more of diastolic blood pressure), (3) elevated blood glucose (110 mg/dL or more of fasting blood glucose level), were classified into the "metabolic syndrome group", subjects having one item from the group were classified into the "pre metabolic syndrome group", and the remaining subjects were classified into the "normal human group".

Average values of serum plasmalogen amount, CP amount, EP amount, CP/PL(Phospholipid), CP/Body weight, CP/triglyceride, CP/EP, C18:1 CP amount, C18:1 CP/PL(Phospholipid), C18:1 CP/triglyceride, C18:1 CP/Body weight, C18:2 CP amount, C18:2 CP/PL(Phospholipid), C18:2 CP/triglyceride, and C18:2 CP/Body weight of the above three groups are shown in Table 5.

The main fatty acid at the sn-2 position of plasmalogen was C20:4 (arachidonic acid). Thus, C20:4 CP amount, C20:4 CP/PL(Phospholipid), C20:4 CP/triglyceride, and C20:4 CP/Body weight also were measured and calculated. Further, each value of the "normal human group" is scaled to be 1, and the relative values of the above items with respect to each value of the "normal human group", are shown in Table 6.

Among the serum plasmalogens, C20:4 (i.e. plasmalogen having arachidonic acid at the sn-2 position) was 33.8%, C18:2 was 20.8%, and C18:1 was 6.4%.

TABLE 5

| | Normal human | Metabolic syndrome | Pre metabolic syndrome |
|---|---|---|---|
| Serum plasmalogen(μM) | 140.9 | 136.7 | 133.3 |
| EP amount(μM) | 75.1 | 80.3 | 72.5 |
| CP amount(μM) | 65.9 | 56.5 | 60.8 |
| CP/Phospholipid(μM/mM) | 21.6 | 16.5 | 19.5 |
| CP/Body weight(μM/kg) | 1.06 | 0.72 | 0.78 |
| CP/Triglyceride (μM/(mg/dL)) | 0.91 | 0.32 | 0.65 |
| CP/EP(μM/μM) | 0.91 | 0.72 | 0.86 |
| C18:1CP(μM) | 6.3 | 4.8 | 5.6 |
| C18:1CP/Phospholipid(μM/mM) | 0.21 | 0.14 | 0.18 |
| C18:1CP/Triglyceride (μM/(mg/dL)) | 0.088 | 0.028 | 0.061 |
| C18:1CP/Body weight(μM/kg) | 0.103 | 0.061 | 0.072 |
| C18:2CP(μM) | 19.3 | 15.2 | 17.9 |
| C18:2CP/Phospholipid(μM/mM) | 0.63 | 0.44 | 0.58 |
| C18:2CP/Triglyceride(μM/(mg/dL)) | 0.27 | 0.09 | 0.19 |
| C18:2CP/Body weight(μM/kg) | 0.31 | 0.19 | 0.23 |

TABLE 6

| | Measurement value | | |
|---|---|---|---|
| | Normal human (A) | Metabolic syndrome (B) | (B)/(A) |
| C18:1CP(μM) | 6.3 | 4.8 | 0.76 |
| C18:2CP(μM) | 19.3 | 15.2 | 0.79 |
| C20:4CP(μM) | 19.6 | 18.2 | 0.92 |
| C18:1CP/Phospholipid(μM/mM) | 0.21 | 0.14 | 0.67 |
| C18:2CP/Phospholipid(μM/mM) | 0.63 | 0.44 | 0.70 |
| C20:4CP/Phospholipid(μM/mM) | 0.64 | 0.53 | 0.82 |
| C18:1CP/Triglyceride (μM/(mg/dL)) | 0.088 | 0.028 | 0.32 |
| C18:2CP/Triglyceride (μM/(mg/dL)) | 0.27 | 0.09 | 0.32 |
| C20:4CP/Triglyceride (μM/(mg/dL)) | 0.27 | 0.10 | 0.37 |
| C18:1CP/Body weight(μM/kg) | 0.103 | 0.061 | 0.59 |
| C18:2CP/Body weight(μM/kg) | 0.31 | 0.19 | 0.62 |
| C20:4CP/Body weight(μM/kg) | 0.31 | 0.23 | 0.73 |

There was little difference found in the serum plasmalogen amount and EP amount among the three groups. On the other hand, there were significant differences found in other makers. There were more significant differences found in the markers associated with C18:1 CP amount or C18:2 CP amount, in particular the C18:1 CP amount, compared to the markers associated with CP amount. Further, there were more clear differences in the order of the ratio of the above amounts to triglyceride, the ratio of the above amounts to body weight, and the ratio of the above amounts to phospholipid. There was a difference found in EP/CP, as well as other markers, between the "metabolic syndrome group" and the "normal human group", but there was little difference found in EP/CP between the "pre-metabolic syndrome group" and the "normal human group". Therefore, the EP/CP ratio was inferior to other markers, in terms of an expectation of the symptoms of metabolic syndrome.

Further, values of (B)/(A) were significantly low in markers associated with C18:1 CP amount or C18:2 CP amount, in particular C18:1 CP amount, compared to the markers associated with C20:4 CP amount. Therefore, it was found that there were significant differences in markers associated with C18:1 CP amount or C18:2 CP amount between the "metabolic syndrome group" and the "normal human group".

INDUSTRIAL APPLICABILITY

The method and kit for detecting metabolic syndrome or life-style related disease of the present invention can be used as a marker for detecting metabolic syndrome or life-style related disease in health checkups and the like.

Although the present invention has been described with reference to specific embodiments, various changes and modifications obvious to those skilled in the art are possible without departing from the scope of the appended claims.

The invention claimed is:

1. A method for detecting a metabolic syndrome or a life-style related disease the method comprising:

(1) measuring a concentration of a choline plasmalogen in a human sample, wherein at least one compound selected from the group consisting of 1-alkenyl cyclic phosphatidic acid of the general formula (1):

(1)

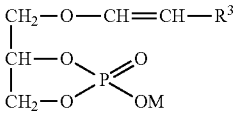

wherein $R^3$ is an alkyl group having 4 to 26 carbon atoms or an alkenyl group having 4 to 26 carbon atoms, and M is a hydrogen atom or a counter cation, and a compound of the general formula (2):

(2)

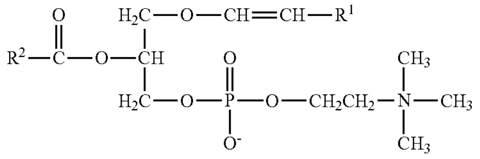

wherein $R^1$ is an alkyl group having 7, 9, 11, 13, 15, 17, 19, or 21 carbon atoms, and $R^2$ is an alkyl group having 8 to 21 carbon atoms or an alkenyl group having 8 to 21 carbon atoms, is used as an internal standard material for measuring the concentration of the choline plasmalogen, and (2) comparing the concentration of the choline plasmalogen measured in step (1) with a reference value of a normal human sample.

2. The method of claim 1, wherein the choline plasmalogen is a choline plasmalogen having oleic acid at the sn-2 position or a choline plasmalogen having linoleic acid at the sn-2 position.

3. The method of claim 1, further comprising:

measuring at least one value selected from the group consisting of a phospholipid concentration in the human sample, a neutral fat concentration in the human sample, and a body weight of a subject; and calculating a ratio between the concentration of choline plasmalogen measured in step (1), and the phospholipid concentration, the neutral fat concentration, or the body weight of the subject.

4. The method of claim 1, the life-style related disease is selected from the group consisting of dyslipidemia, hypertension, and arteriosclerosis.

5. A kit for detecting a metabolic syndrome or a life-style related disease, comprising a 1-alkenyl cyclic phosphatidic acid of the general formula (1):

(1)

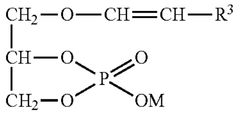

wherein $R^3$ is an alkyl group having 4 to 26 carbon atoms or an alkenyl group having 4 to 26 carbon atoms, and M is a hydrogen atom or a counter cation, as an internal standard material for measuring a concentration of a choline plasmalogen, and an extraction agent for extracting the choline plasmalogen from a human sample.

6. A kit for detecting a metabolic syndrome or a life-style related disease, comprising a compound of the general formula (2):

(2)

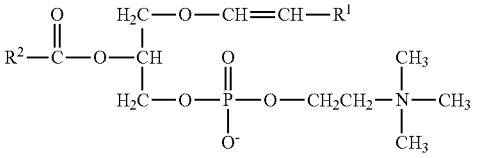

wherein $R^1$ is an alkyl group having 7, 9, 11, 13, 15, 17, 19, or 21 carbon atoms, and $R^2$ is an alkyl group having 8 to 21 carbon atoms or an alkenyl group having 8 to 21 carbon atoms, as an internal standard material for measuring a concentration of a choline plasmalogen, and an extraction agent for extracting the choline plasmalogen from a human sample.

* * * * *